(12) United States Patent
Arbefeuille (10) Patent No.: US 11,219,540 B2
(45) Date of Patent: Jan. 11, 2022

(54) RADIALLY ADJUSTABLE STENT GRAFT DELIVERY SYSTEM AND METHOD OF USE

(71) Applicant: Bolton Medical, Inc., Sunrise, FL (US)

(72) Inventor: Samuel Arbefeuille, Sunrise, FL (US)

(73) Assignee: Bolton Medical, Inc., Sunrise, FL (US)

(*) Notice: Subject to any disclaimer, the term of this patent is extended or adjusted under 35 U.S.C. 154(b) by 190 days.

(21) Appl. No.: 16/414,132

(22) Filed: May 16, 2019

(65) Prior Publication Data

US 2019/0269537 A1 Sep. 5, 2019

Related U.S. Application Data

(63) Continuation of application No. PCT/US2018/019356, filed on Feb. 23, 2018.

(Continued)

(51) Int. Cl.
*A61F 2/95* (2013.01)
*A61F 2/07* (2013.01)
(Continued)

(52) U.S. Cl.
CPC .............. *A61F 2/95* (2013.01); *A61F 2/07* (2013.01); *A61M 25/09* (2013.01); *A61F 2/90* (2013.01); *A61F 2/9517* (2020.05); *A61F 2/9522* (2020.05); *A61F 2002/075* (2013.01); *A61F 2002/826* (2013.01); *A61F 2002/9505* (2013.01); *A61F 2002/9511* (2013.01); *A61F 2210/0014* (2013.01); *A61M 25/10* (2013.01); *A61M 2025/09008* (2013.01)

(58) Field of Classification Search
CPC .. A61F 2/95; A61F 2/07; A61F 2/9517; A61F 2/9522; A61F 2002/9511; A61F 2002/826; A61F 2002/075; A61F 2/90; A61F 2002/9505; A61F 2210/0014; A61M 25/09; A61M 25/10; A61M 2025/09008

See application file for complete search history.

(56) References Cited

U.S. PATENT DOCUMENTS

| 5,123,917 A | 6/1992 | Lee |
| 5,507,769 A | 4/1996 | Marin et al. |

(Continued)

FOREIGN PATENT DOCUMENTS

| CN | 105832447 A | 8/2016 |
| EP | 0786972 B1 | 1/2004 |

(Continued)

OTHER PUBLICATIONS

International Preliminary Report on Patentability for International Application No. PCT/US2018/019356 dated Aug. 27, 2019.

(Continued)

*Primary Examiner* — Jerrah Edwards
*Assistant Examiner* — Jared Klar Rovira
(74) *Attorney, Agent, or Firm* — Foley Hoag LLP (57) ABSTRACT

A stent graft delivery system and method for implanting a stent graft includes and employs at least one control rod that extends along a luminal wall of a stent graft and at least one ligature. The ligature extends about radial stents. Rotation of the control rod or a tube extending about the control rod wraps the ligature about the control rod, thereby radial constricting the stent about which the ligature extends.

23 Claims, 12 Drawing Sheets

Related U.S. Application Data (60) Provisional application No. 62/463,066, filed on Feb. 24, 2017.

(51) Int. Cl.

| | | |
|---|---|---|
| *A61M 25/09* | (2006.01) | |
| *A61F 2/90* | (2013.01) | |
| *A61M 25/10* | (2013.01) | |
| *A61F 2/82* | (2013.01) | |

(56) References Cited

U.S. PATENT DOCUMENTS

| | | |
|---|---|---|
| 5,755,769 A | 5/1998 | Richard et al. |
| 5,873,906 A | 2/1999 | Lau et al. |
| 6,113,623 A | 9/2000 | Sgro |
| 6,171,334 B1 | 1/2001 | Cox |
| 6,280,464 B1 | 8/2001 | Hayashi |
| 6,395,018 B1 | 5/2002 | Castaneda |
| 7,435,253 B1 | 10/2008 | Hartley et al. |
| 7,637,940 B2 | 12/2009 | Kocur et al. |
| 7,763,063 B2 | 7/2010 | Arbefeuille et al. |
| 8,007,605 B2 | 8/2011 | Arbefeuille et al. |
| 8,172,895 B2 | 5/2012 | Anderson et al. |
| 8,236,040 B2 | 8/2012 | Mayberry et al. |
| 8,480,725 B2 | 7/2013 | Rasmussen et al. |
| 8,486,129 B2 | 7/2013 | Lautherjung |
| 8,500,792 B2 | 8/2013 | Berra |
| 8,641,752 B1 | 2/2014 | Holm et al. |
| 8,808,351 B2 | 8/2014 | Osborne |
| 8,926,693 B2 * | 1/2015 | Duffy .................. A61F 2/2436 623/2.11 |
| 9,101,455 B2 | 8/2015 | Roeder et al. |
| 9,101,506 B2 | 8/2015 | Arbefeuille et al. |
| 9,259,336 B2 | 2/2016 | Schaeffer et al. |
| 9,364,314 B2 | 6/2016 | Berra et al. |
| 9,375,308 B2 | 6/2016 | Norris |
| 9,439,751 B2 | 9/2016 | White et al. |
| 9,592,112 B2 | 3/2017 | Arbefeuille et al. |
| 9,827,123 B2 | 11/2017 | Arbefeuille et al. |
| 9,861,503 B2 | 1/2018 | Barthold et al. |
| 9,877,857 B2 | 1/2018 | Arbefeuille et al. |
| 9,913,743 B2 | 3/2018 | Arbefeuille et al. |
| 10,005,269 B2 | 6/2018 | Hall et al. |
| 10,080,674 B2 | 9/2018 | Yuan et al. |
| 10,299,951 B2 | 5/2019 | Arbefeuille et al. |
| 10,390,930 B2 | 8/2019 | Arbefeuille et al. |
| 10,617,542 B2 | 4/2020 | Chakfe et al. |
| 10,898,357 B2 | 1/2021 | Arbefeuille et al. |
| 2002/0062133 A1 | 5/2002 | Gilson et al. |
| 2002/0177890 A1 | 11/2002 | Lenker |
| 2002/0188344 A1 | 12/2002 | Bolea et al. |
| 2002/0193872 A1 | 12/2002 | Trout et al. |
| 2004/0073289 A1 | 4/2004 | Hartley |
| 2005/0119722 A1 | 6/2005 | Styrc et al. |
| 2005/0131517 A1 | 6/2005 | Hartley et al. |
| 2005/0131518 A1 | 6/2005 | Hartley et al. |
| 2005/0131519 A1 | 6/2005 | Hartley |
| 2005/0131523 A1 | 6/2005 | Bashiri et al. |
| 2006/0015171 A1 | 1/2006 | Armstrong |
| 2006/0020319 A1 | 1/2006 | Kim et al. |
| 2006/0184226 A1 | 8/2006 | Austin |
| 2007/0055360 A1 | 3/2007 | Hanson et al. |
| 2007/0135904 A1 | 6/2007 | Eidenschink et al. |
| 2007/0213805 A1 | 9/2007 | Schaeffer et al. |
| 2008/0091260 A1 | 4/2008 | Pomeranz et al. |
| 2008/0269867 A1 | 10/2008 | Johnson |
| 2010/0004730 A1 | 1/2010 | Benjamin et al. |
| 2010/0234932 A1 | 9/2010 | Arbefeuille et al. |
| 2010/0316830 A1 | 12/2010 | Hartley et al. |
| 2011/0190862 A1 | 8/2011 | Bashiri et al. |
| 2011/0257720 A1 | 10/2011 | Peterson et al. |
| 2012/0221096 A1 | 8/2012 | Roeder et al. |
| 2012/0271401 A1 | 10/2012 | Bruszewski et al. |
| 2013/0116773 A1 | 5/2013 | Roeder et al. |
| 2013/0116775 A1 | 5/2013 | Roeder et al. |
| 2013/0123900 A1 | 5/2013 | Eblacas et al. |
| 2013/0158648 A1 | 6/2013 | Hartley et al. |
| 2013/0184806 A1 | 7/2013 | Arbefeuille et al. |
| 2013/0282102 A1 | 10/2013 | Peterson |
| 2013/0289713 A1 | 10/2013 | Pearson et al. |
| 2014/0039597 A9 | 2/2014 | Arbefeuille et al. |
| 2014/0046428 A1 | 2/2014 | Cragg et al. |
| 2014/0180378 A1 | 6/2014 | Roeder |
| 2015/0105819 A1 | 4/2015 | Becking et al. |
| 2015/0105849 A1 | 4/2015 | Cohen et al. |
| 2015/0202065 A1 | 7/2015 | Shalev et al. |
| 2015/0202067 A1 | 7/2015 | Barrand et al. |
| 2015/0272755 A1 | 10/2015 | Arbefeuille et al. |
| 2015/0335452 A1 | 11/2015 | Rao et al. |
| 2016/0184078 A1 | 6/2016 | Choubey et al. |
| 2016/0199207 A1 | 7/2016 | Treacy et al. |
| 2016/0296353 A1 | 10/2016 | Skender |
| 2016/0302950 A1 | 10/2016 | Marmur et al. |
| 2017/0135807 A1 | 5/2017 | Arbefeuille et al. |
| 2017/0281382 A1 | 10/2017 | Lostetter et al. |
| 2018/0071123 A1 | 3/2018 | Arbefeuille et al. |
| 2018/0296374 A1 | 10/2018 | Chakfe et al. |
| 2019/0350694 A1 | 11/2019 | Arbefeuille et al. |
| 2021/0100669 A1 | 4/2021 | Arbefeuille et al. |

FOREIGN PATENT DOCUMENTS

| | | | |
|---|---|---|---|
| EP | 1847234 A1 | 10/2007 | |
| EP | 1847236 A2 | 10/2007 | |
| EP | 2471498 A1 * | 7/2012 | ............ A61F 2/962 |
| EP | 2517672 A1 | 10/2012 | |
| EP | 2735283 A1 * | 5/2014 | ............... A61F 2/07 |
| EP | 2740440 A2 | 6/2014 | |
| EP | 2745812 A1 * | 6/2014 | ............... A61F 2/07 |
| EP | 2745813 A1 * | 6/2014 | ............ A61F 2/966 |
| EP | 2749250 A1 | 7/2014 | |
| EP | 2749251 A1 | 7/2014 | |
| EP | 3040054 A1 | 7/2016 | |
| EP | 3068339 A1 | 9/2016 | |
| EP | 3146993 A1 | 3/2017 | |
| EP | 3272319 A1 | 1/2018 | |
| FR | 2932979 A1 | 1/2010 | |
| GB | 2464978 A | 5/2010 | |
| WO | WO-97/03624 A1 | 2/1997 | |
| WO | WO-01/60285 A1 | 8/2001 | |
| WO | WO-02/083038 A2 | 10/2002 | |
| WO | WO-2005/034809 A1 | 4/2005 | |
| WO | WO-2006/037086 A1 | 4/2006 | |
| WO | WO-2009/148594 A1 | 12/2009 | |
| WO | WO-2010/024880 A1 | 3/2010 | |
| WO | WO-2010/030370 A1 | 3/2010 | |
| WO | WO-2010/127040 A1 | 11/2010 | |
| WO | WO-2012/116368 A2 | 8/2012 | |
| WO | WO-2012/145823 A1 | 11/2012 | |
| WO | WO-2014/149022 A1 | 9/2014 | |
| WO | WO-2015/070792 A1 | 5/2015 | |
| WO | WO-2016/122862 A1 | 8/2016 | |
| WO | WO-2017/218474 A1 | 12/2017 | |
| WO | WO-2018/026768 A1 | 2/2018 | |

OTHER PUBLICATIONS

International Search Report and Written Opinion for International Application No. PCT/US2018/019356 dated May 16, 2018.

* cited by examiner

RADIALLY ADJUSTABLE STENT GRAFT DELIVERY SYSTEM AND METHOD OF USE

RELATED APPLICATION

This application is a continuation of International Application No. PCT/US2018/019356, which designated the United States and was filed on Feb. 23, 2018, published in English, which claims the benefit of U.S. Provisional Application No. 62/463,066, filed on Feb. 24, 2017. The entire teachings of the above applications are incorporated herein by reference.

BACKGROUND

Arterial pathologies, including aortic aneurysms, can be treated by open surgical reconstruction, or alternatively, endovascular repair, which is a minimally invasive alternative to open surgical repair. Optimizing a successful outcome of endovascular repair, however, requires assessment of the patient's anatomy and, in the case of an aortic aneurysm, selection of an appropriate stent graft that spans the proximal and distal ends of the aneurysm to insure complete exclusion of the aneurysm sac, anchoring of the stent graft in the aorta, and minimal endoleaks. Also, endoleaks and post-surgical enlargement of the aneurysm site can require additional repair to seal any expansion of the aneurysm sac, and, generally, must be done without significantly compromising blood flow through the surgical site to surrounding viscera and associated structures.

Therefore, a need exists for new and improved endovascular repair devices and methods to treat aortic pathologies, in particular aortic aneurysms.

SUMMARY

The present invention relates to a stent graft delivery system and a method for its use in treating and repairing aortic vascular damage, such as vascular damage associated with aortic aneurysms, in regions of the aorta having arterial branches that supply blood to vital organs and tissues, such as thoracic abdominal aortic aneurysms, abdominal aortic aneurysms and thoracoabdominal aortic aneurysms, including juxtarenal aortic aneurysms and short-neck aortic aneurysms.

In one embodiment, the invention is a stent graft delivery system that includes a stent graft having a luminal graft component with an outside surface, an inside surface, a proximal open end, a distal open end, and defining a lumen therebetween. The stent graft also includes a plurality of stents extending longitudinally along the luminal wall. A control rod extends longitudinally along the luminal graft component, and at least one ligature traverses at least one of the stents, and is controllably and releasably fixed to the control rod, whereby control of the ligature at the control rod radially constricts the traversed stent.

In another embodiment, the invention is a method for treating an arterial aneurysm. In an embodiment, the arterial aneurysm is an aortic aneurysm. A stent graft of a stent graft delivery system is located to an arterial aneurysm of a patient. The stent graft delivery system includes a stent graft having a luminal graft component having an outside surface, an inside surface, a proximal open end, a distal open end, and defining a lumen, and also including a plurality of stents extending longitudinally along the luminal wall. A control rod of the stent graft delivery system extends longitudinally along the luminal graft component, at least one ligature traversing at least one of the stent. The ligature is controllably and releasably fixed to the control rod, whereby selective control at the control rod radially constricts the stent traversed by the at least one ligature. The stent graft is positioned at the aneurysm site by controlling the ligature to radially constrict the stent traversed by the at least one ligature. The ligature is released from the control rod, releasing the stent graft and thereby treating the arterial aneurysm.

This invention has many advantages. For example, where the radially constricted stent is radially self-expanding, or is radially constrained in opposition to some other radially expanding force, such as a balloon catheter, as is known in the art, the physician can rotate or reposition the stent graft after it has been at least partially radially expanded, such as by only partially relaxing or reconstructing or reconstraining a ligature extending about stents of the stent graft by rotational movement of a control rod in which the ligature is wrapped. Axial or longitudinal repositioning of the reconstrained stent graft, or a portion thereof, provides greater control over delivery systems that are only able to position the stent graft prior to full expansion of the stent graft within a blood vessel. As a consequence, a stent graft can be deployed at a surgical site with more accuracy, less risk of injury to the vasculature of the subject, and without significant risk of distorting the intended shape of the stent graft when implanted at the surgical site.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments. The same number in different drawings represents the same item.

DETAILED DESCRIPTION

A description of example embodiments follows.

The invention is generally directed to a stent graft delivery system that includes at least one control rod and at least one ligature that is releasably fixed to the control rod and about a stent of a stent graft. The invention also is directed to a method of use of the delivery system of the invention. The stent graft delivery system and method are used to treat aortic vascular damage, such as vascular damage associated with an aortic aneurysms, including in regions of the aorta having arterial branches that supply blood to vital organs and tissues, such as juxtarenal aortic aneurysms and short-neck abdominal aortic aneurysms.

When reference is made herein to a prosthesis, also referred to herein as "stent graft," "stent graft prosthesis," or "vascular prosthesis," to be delivered, or implanted in a patient, the word "proximal" means that portion of the prosthesis or component of the prosthesis that is relatively close to the heart of the patient and "distal" means that portion of the prosthesis or component of the prosthesis that is relatively far from the heart of the patient.

When, however, reference is made to a delivery system or a component of a delivery system employed to deliver, or implant, a prosthesis, the word, "proximal," as employed herein, means closer to the clinician using the delivery system. When reference is made to a delivery system or a component of a delivery system, "distal," as that term is employed herein, means, further away from the clinician using the delivery system.

For clarity, the word "proximate" means "close to," as opposed to the meanings ascribed to "proximal" or "distal" described above with respect to either the prosthesis or a delivery system.

Figure 1A:
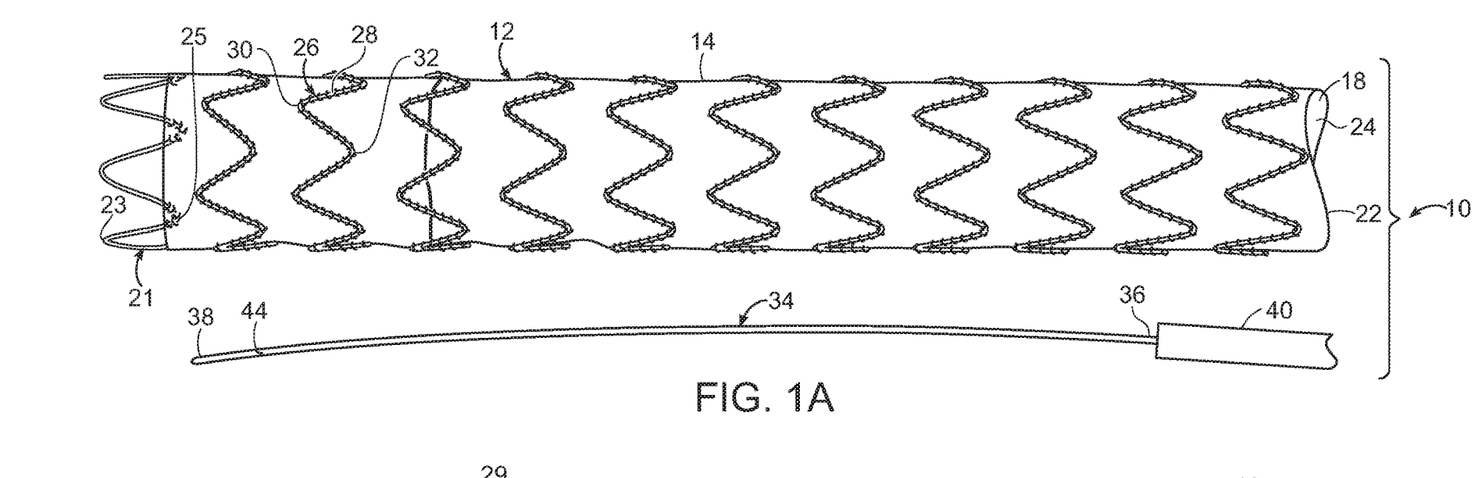
FIG. 1A is an exploded side view of one embodiment of a stent graft delivery system of the invention, having a ligature traversing struts of a radial stent, and a control rod, shown separately from the stent graft and ligature.
Figure 1B:
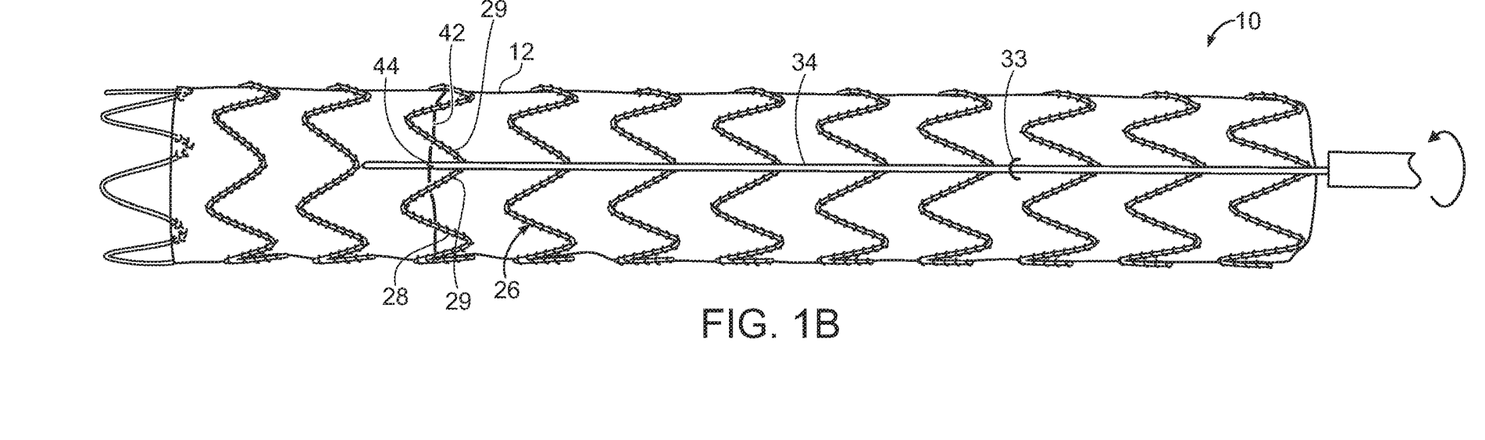
FIG. 1B is a side view of the stent graft delivery system shown in FIG. 1A, when assembled.

In one embodiment, the invention is a stent graft delivery system, such as is shown in FIGS. 1A and 1B. As can be seen in FIG. 1A, stent graft delivery system 10 includes stent graft 12. Stent graft 12 includes luminal graft component 14 having outside surface 16, inside surface 18, proximal open end 20, distal open end 22, and defines lumen 24. A plurality of radial stents 26 extend longitudinally along luminal graft component 14. Stents 26 include struts 28 that are joined at opposite ends to thereby define proximal apices 30 and distal apices 32. Bare stent 21 is at proximal open end 20 and includes proximal apices 23 and distal apices 25. In an embodiment, at least one of proximal apices 23 and distal apices 32 include barbs extending distally from bridge of eyelet (not shown). It is to be understood that in embodiments, the proximal open ends of stent grafts of the delivery systems of the invention can be without bare stents (not shown). Control rod 34 includes proximal end 36 and distal end 38. Control rod handle 40 is fixed to proximal end 36 of control rod 34.

Figure 1C:
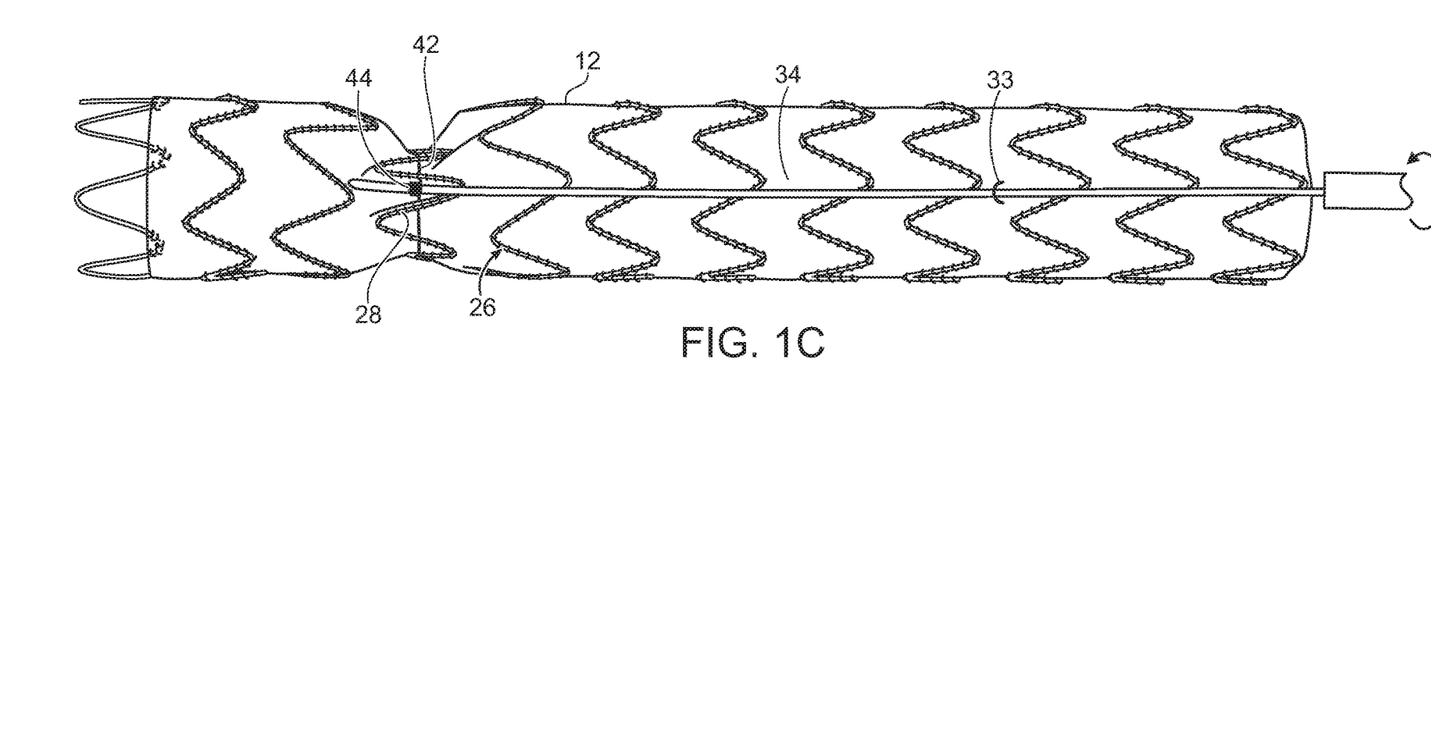
FIG. 1C is a side view of the embodiment of the stent graft delivery system shown in FIGS. 1A and 1B, wherein the control rod has been axially rotated to wrap the ligature about the control rod and thereby radially constrict the stent graft at the ligature.

As shown in FIG. 1B, control rod 34 extends longitudinally along stent graft 12 at least one of distal apices. Ligature 42 traverses radial stent 26 and is controllably and releasably fixed to the control rod 34. In the embodiment, shown in FIGS. 1A and 1B, ligature 42 extends through notch 44 in control rod 34, and traverses struts 28 of radially self-expanding stent 26, whereby, according to one embodiment of a method of the invention, and as can be seen in FIG. 1C, rotation of control rod 34 at ligature 42 causes ligature 42 to wrap about the control rod 34, thereby radially constricting the at least one radial stent 26 traversed by ligature 42. Optionally, loop 33 secures control rod 34 to luminal graft component 14. In an embodiment, ligature 42 passes under a portion of struts 28 of stent 26. In another embodiment, ligature 42 cover struts 29 on either side of control rod 34 (not shown) and remaining portion of ligature 42 passes under remaining struts 28 of stent 26.

In one embodiment, radial stent 26 at ligature 42 is radially self-expanding, or is radially constrained in opposition to some other radially expanding force, such as a balloon catheter (not shown) as is known in the art. Radially self-expanding stents include those that are fabricated of, for example, a shape memory alloy, such as Nitinol. Examples of other suitable materials of fabrication of stents 26 include stainless steel and a suitable polymer. Ligature 42 and loop 33 are formed of a suitable material, such as is known in the art, including polyester, nylon, and polypropylene.

Figure 2A:
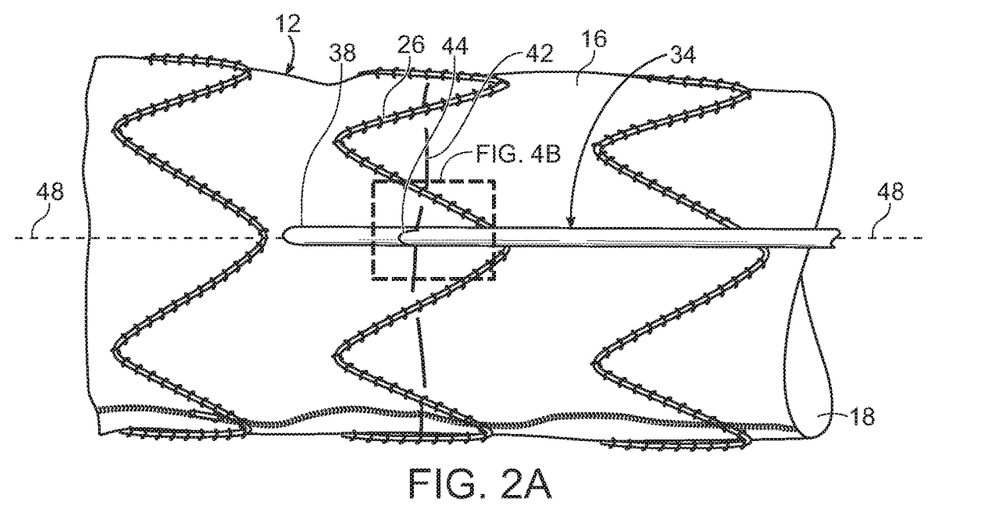
FIG. 2A is a detail of a distal end of the control rod and stent graft of FIGS. 1A-1C, wherein the ligature traversing the struts of the radial stent is releasably fixed to the control rod by engagement with a notch at the control rod.
Figure 2B:
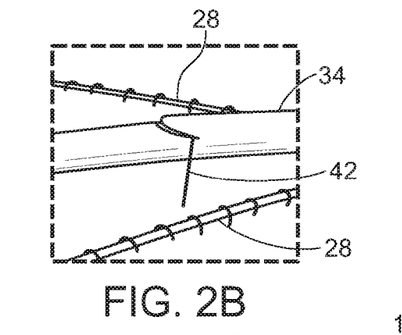
FIG. 2B is a detail of the notch and releasable engagement of the ligature at the notch of the control rod shown in FIG. 2A.
Figure 2C:
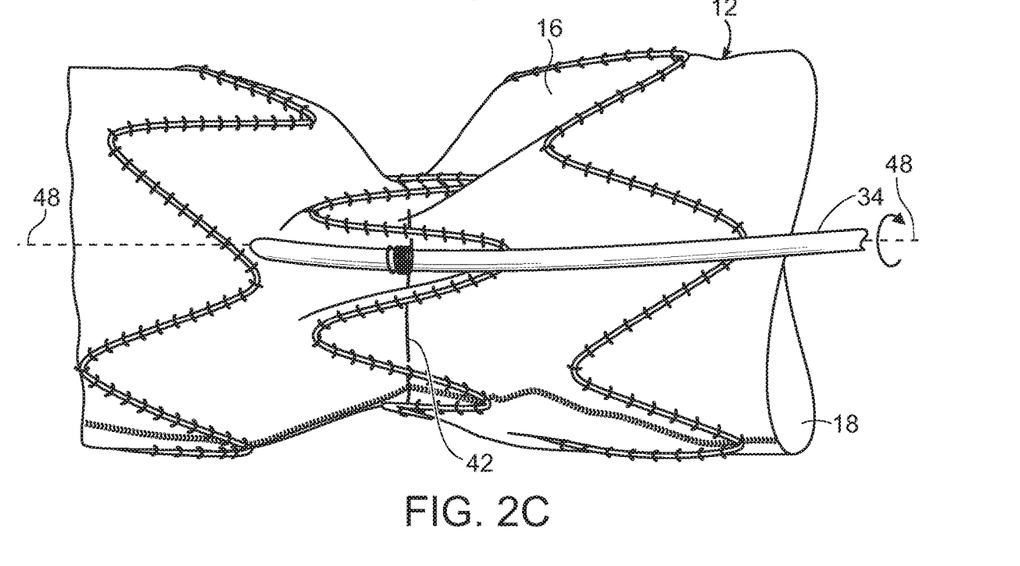
FIG. 2C is a representation of the embodiment shown in FIGS. 1A-1C, 2A, and 2B, wherein the control rod has been rotated about its longitudinal axis to thereby wrap the ligature about the control rod and thereby radially constrict the stent graft at the stent traversed by the ligature.
Figure 2D:
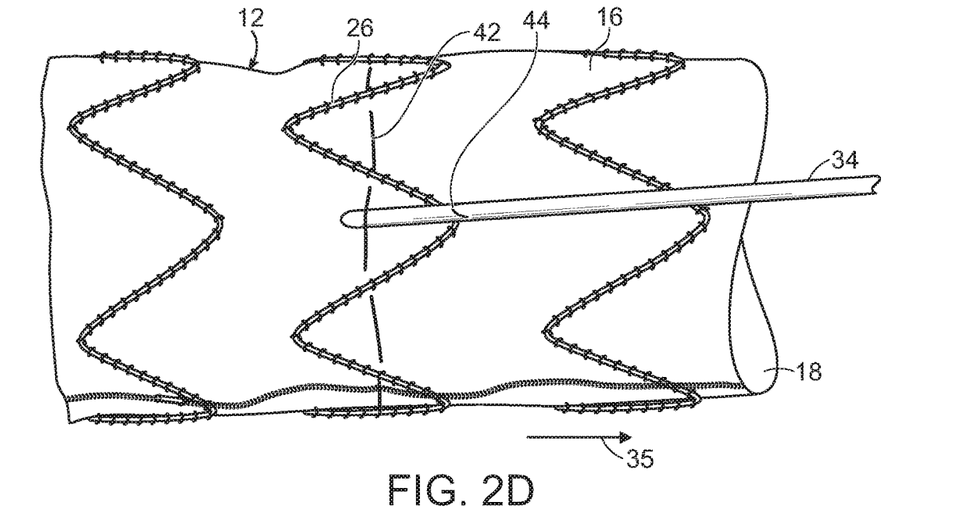
FIG. 2D is the stent graft represented in FIGS. 1A-1C and 2A-2C, following relaxation of tension on the ligature, thereby the allowing the radial stent of the stent graft to radially expand, such as where the radial stent is radially self-expanding, and following release of the ligature from the notch of the control rod by retraction of the control rod from the ligature.

FIG. 2A is a detail of the embodiment shown in FIG. 1B, showing notch 44 defined by control rod 34 at distal end 38, and wherein ligature 42 traverses notch 44, as more clearly shown in detail in FIG. 2B, whereby rotation of control rod 34 causes ligature 42 to be releasably fixed to control rod 34 and thereby cause ligature 42 to wrap around control rod 34 by rotation of control rod 34, about its longitudinal axis 48, as shown in FIG. 2C. Wrapping of ligature 42 about control rod 34 causes constriction of radially self-expanding stent 26. As also shown in FIGS. 2A-2C, ligature 42 traverses struts 28 attached to outside surface 16 of stent graft 12. In this embodiment, ligature 42 penetrates luminal graft component 14 on either lateral side of strut 28, whereby ligature 42 traverses strut 28 while passing across inside surface 18 of luminal graft component 14. Release of control rod 34 allows ligature 42 to unwind from control rod 34 by expansion of radial stent 26, such as by radial self expansion of stent 26 where stent 26 is fabricated of a suitable shape memory alloy, such as Nitinol. Alternatively, control rod 34 can be rotated in the opposite direction to thereby allow expansion of stent 26 which, in yet another embodiment, can be a stent that does not radially self-expand, but, rather, expands by virtue of some other mechanism known in the art, such as a balloon catheter (not shown). In any case, the position of stent 26, ligature 42 and control rod 34 can return to that shown in FIGS. 2A and 2B following at least one of axial and longitudinal positioning of stent graft 12 at an arterial aneurysm. It is to be understood that the radial expansion and radial constriction of stent 26 can be variably controlled by control rod 34 until at least one of axial and longitudinal positioning is complete. Control rod 34 is then separated from ligature 42. Ligature 42 is released from control rod 34 and control rod 34 can be removed from the stent graft 12 at the arterial aneurysm by proximally retracting control rod 34, in the direction indicated by arrow 35 as can be seen in the transition from FIG. 2A through FIG. 2D.

In alternative embodiments, the arrangements of control rod 34, ligature 42 and stents 26 can be varied and still obtain the same result. For example, in one alternative embodiment (not shown), radial stents can be located at inside surface 18 of stent graft 12, rather than, as shown in FIGS. 2A-2D, outside surface 16. In still another embodiment (also not shown) control rod 34 can extend along inside surface 18 of stent graft 12, rather than, as shown in FIGS. 2A-2D, along outside surface 16 of stent graft 12. Still further, the ligature 42, when releasably fixed to control rod 34 extending longitudinally within stent graft 12, can radially constrict stent 12 by passing through luminal graft component 14 of stent graft 12 and traversing struts 26 while passing across outside surface 16 of stent graft.

Figure 3A:
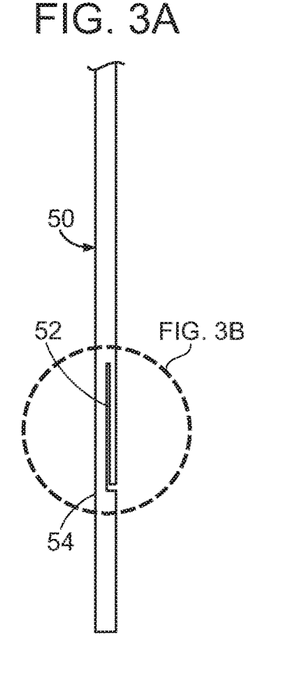
FIG. 3A is a side view of another embodiment of a control rod component of a stent graft delivery system of the invention, wherein the control rod defines a slot running generally longitudinally along the control rod at a distal end, and is accessible at an opening defined by a perimeter of the control rod.
Figure 3B:
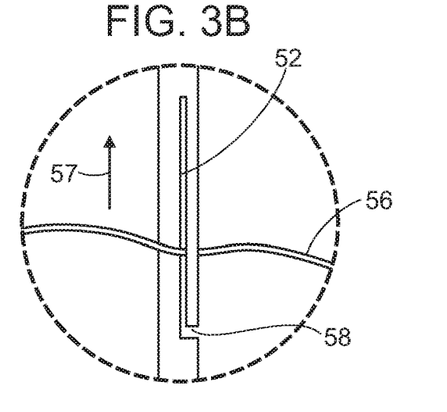
FIG. 3B is a detail of the longitudinal slot when threaded by a ligature, and of the opening to the longitudinal slot defined by the control rod.
Figure 3C:
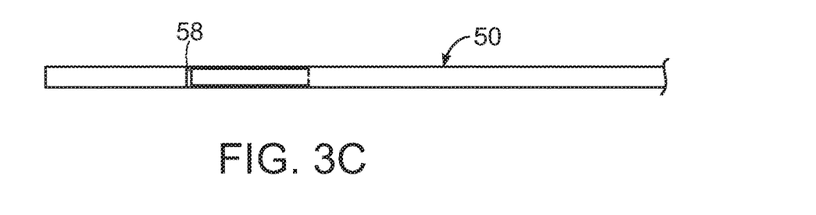
FIG. 3C is a plan view of the control rod shown in FIGS. 3A and 3B showing the opening to the slot of the control rod at the periphery of the control rod.

FIG. 3A is a side view of another embodiment of a control rod of the stent graft delivery system of the invention. As shown in FIG. 3A, control rod 50 defines slot 52 extending generally longitudinally along control rod 50 at distal end 54. Ligature 56 can be captured within slot 52, which is accessible at opening 58 of slot 52 as can be seen in FIG. 3B. Opening 58 of slot 52 is a partial transverse cut at one end of longitudinal slot, as shown in FIGS. 3B and 3C. Rotation of control rod 50 about its longitudinal axis wraps ligature 56 about control rod 50. Ligature 56 can be released from control rod 50 by retracting control rod 50 in a proximal direction, indicated by arrow 57, thereby causing ligature 56 to be drawn out of slot 52 through opening 58.

Figure 4A:
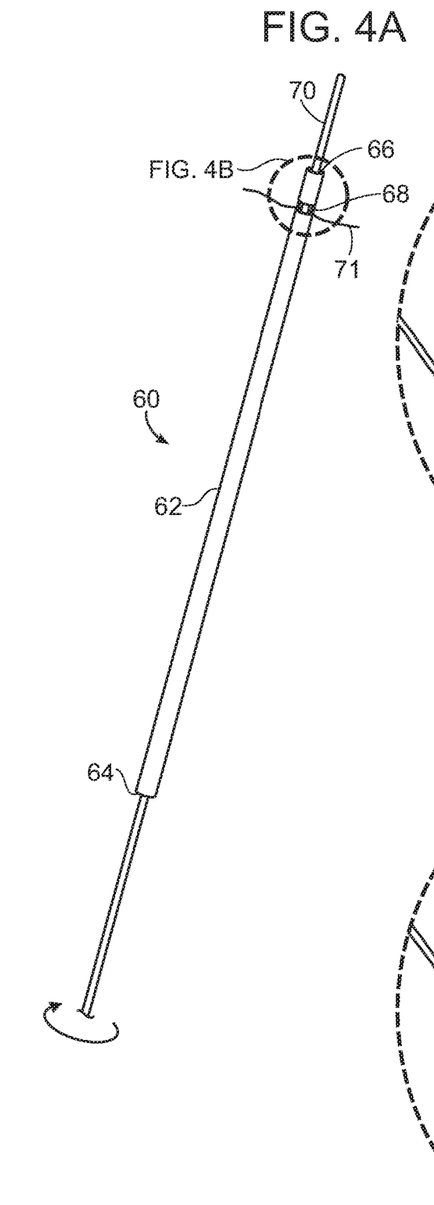
FIG. 4A is a perspective view of yet another embodiment of a control rod component of the stent graft delivery system of the invention, wherein a tube defines a slot, or fenestration, that provides access to a lumen defined by the tube, and a rod or wire that extends through the tube, whereby rotation of the tube while a ligature is threaded between the wire and the tube at the slot causes the ligature to wrap about the tube.
Figure 4B:
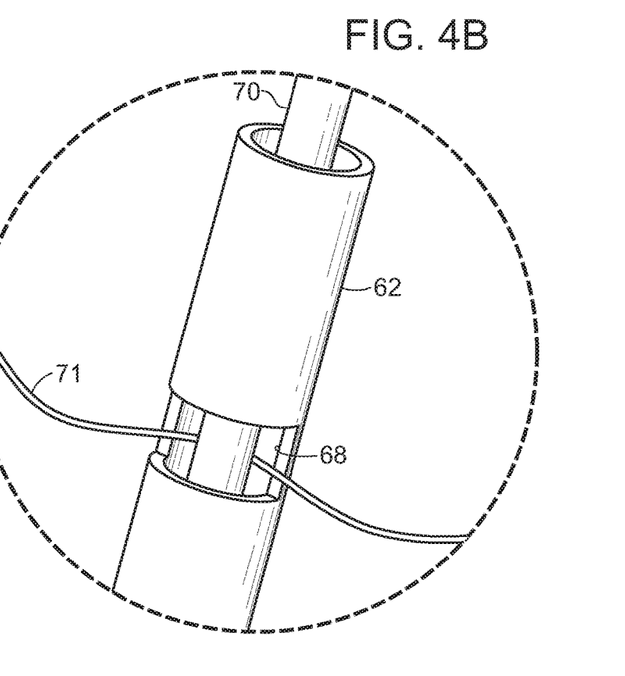
FIG. 4B is a detail of the slot and wire of the control rod shown in FIG. 4A threaded with a suitable ligature.
Figure 4C:
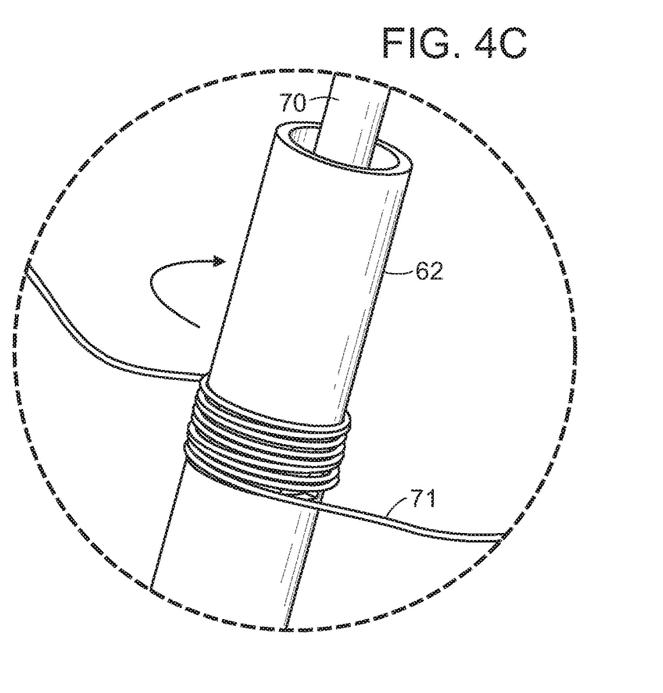
FIG. 4C is a detail of FIG. 4B wherein a ligature has been wrapped around a tube by axial rotation of the tube.

Another embodiment of a control rod is illustrated in FIGS. 4A and 4B. As shown in FIG. 4A, control rod 60 includes tube 62 having proximal end 64 and distal end 66. Slot 68 is at distal end 66. Wire 70 extends longitudinally through tube 62. As can be seen in FIG. 4B, which is a detail taken from FIG. 4A, ligature 71 is threaded between wire 70 and tube 62 at slot 68, whereby rotation of tube 62 about wire 70 causes ligature 71 to wind about the outside surface of tube 62, as shown in FIG. 4C. Ligature 71 can be released from control rod 60 by unwinding ligature from tube 62 and retracting wire 70 from traversing slot 68, or, in some instances, by only proximally retracting wire 70 from traversing slot 68.

Figure 5:
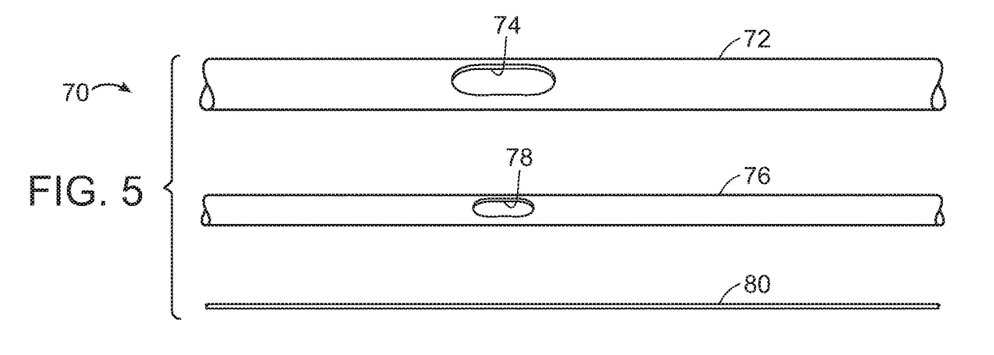
FIG. 5 is a side view of components of still another control rod for use in a stent graft delivery system of the invention, including an outer tube defining an outer tube fenestration, and an inner tube that defines an inner tube fenestration, and a wire.

FIG. 5 is an exploded view of another embodiment of a control rod of a stent graft delivery system of the invention. As shown in FIG. 5, control rod 70 includes outer tube 72 defining outer tube fenestration 74. Inner tube 76 defines inner tube fenestration 78. Inner tube 76 has a diameter smaller than that of an inside diameter of outer tube 72. Wire 80 has a diameter smaller than an interior diameter of inner tube 76. When assembled, as shown in FIG. 6, wire 80 extends longitudinally through the inner tube 76, and inner tube 76 extends longitudinally within outer tube 72, inner tube fenestration 78 is aligned with outer tube fenestration 74, and wire 80 traverses both inner tube fenestration 76 and outer tube fenestration 74.

Figure 6:
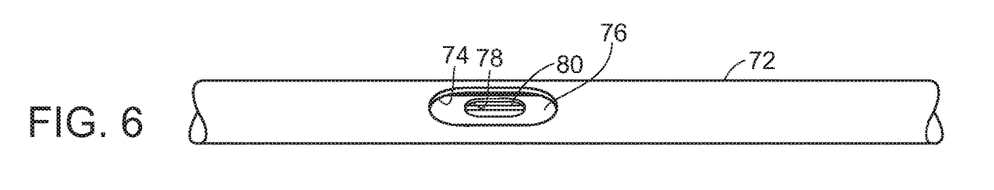
FIG. 6 is a side view of the component parts of the control rod represented in FIG. 5 when assembled, showing the wire running through the inner tube and traversing the inner tube fenestration, and the inner tube being within the outer tube, and wherein the fenestrations of the inner tube and the outer tube are aligned.
Figure 7A:
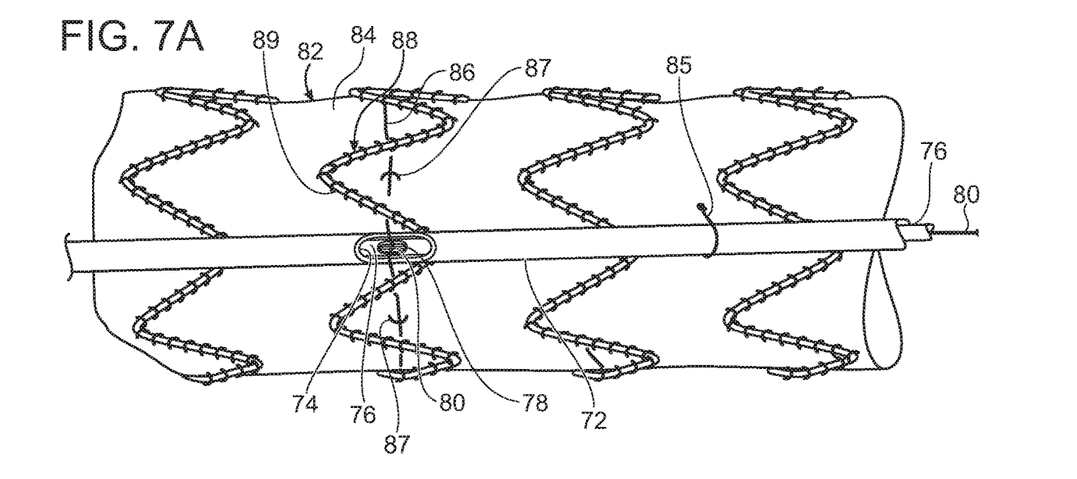
FIG. 7A is a side view of the assembled control rod shown in FIG. 6, wherein a ligature that traverses the struts of a stent of a radial stent graft of the stent graft delivery system of the invention, is threaded between the wire and the inner tube at the inner tube fenestration, and while the inner tube fenestration is aligned with the outer tube fenestration.
Figure 7B:
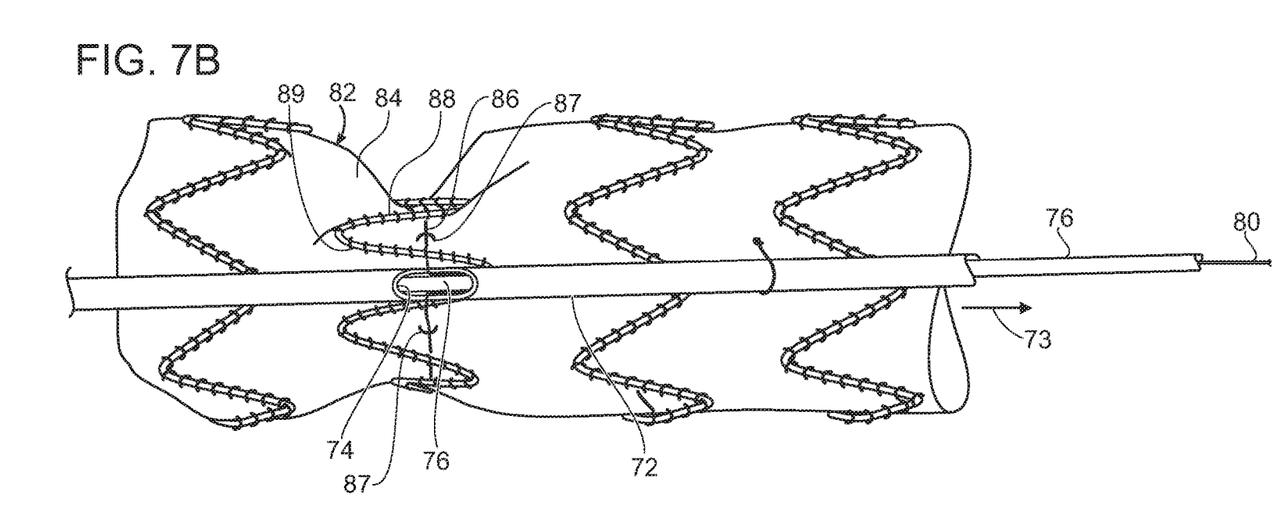
FIG. 7B is a side view of the embodiment shown in FIG. 7A, wherein a stent traversed by a ligature that is linked to the control rod has been radially constricted by proximal retraction of the inner tube relative to the outer tube.

FIG. 7A is a side view of an embodiment of the stent graft delivery system of the invention, wherein control rod 70 of FIGS. 5 and 6 extends longitudinally along stent graft 82 at outside surface 84. Ligature 86 is threaded between wire 80 and an inside surface of inner tube 76 while inner tube fenestration 78 and outer tube fenestration 74 are aligned. Stent 88 of stent graft 82 can be radially constricted by retracting or advancing inner tube 76 within outer tube 72, thereby causing ligature 86 to be drawn within outer tube 72. In an embodiment, ligature 86 is stabilized, at least in part, by at least one ligature suture 87 spanning ligature 86. The arrangement of control rod 70, ligature 86 and stent 88 relative to each other can take different forms, as discussed with respect to the embodiments described above. In one embodiment of a method of the invention, stent 88 is constricted by proximally pulling ligature 86 into the outer tube 72 by retraction of inner tube 76 longitudinally and wire 80 in the direction indicated by arrow 73, if necessary, within outer tube 72, as can be seen in the transition from FIG. 7A to FIG. 7B.

Figure 7C:
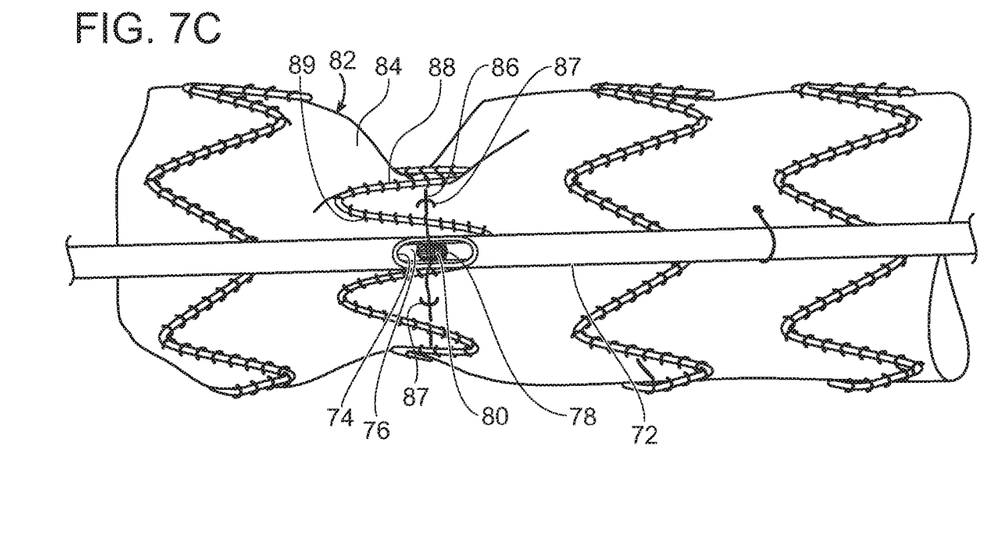
FIG. 7C is a side view of the embodiment shown in FIGS. 7A and 7B, but wherein, rather than proximally retracting the inner tube relative to the outer tube, the stent traversed by the ligature is radially constricted by axially rotating the inner tube of the control rod to thereby wrap the ligature about the inner tube.

In another embodiment of a method of the invention, rather than retracting inner tube 76 and wire 80 within outer tube 72, ligature 86, shown in this embodiment traversing under struts 89 of stent 88, is radially constricted by rotating inner tube 76 to thereby radially constrict stent 88, struts 89 of which are traversed by ligature 86, as can be seen in the transition from FIG. 7A to FIG. 7C.

Figure 8:
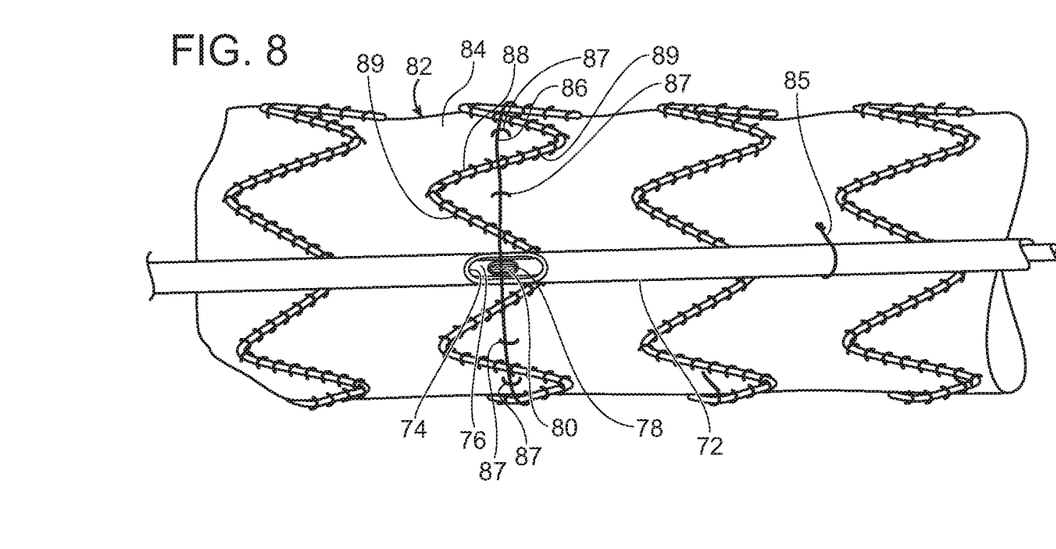
FIG. 8 is a side view of another embodiment of FIG. 7A, wherein the ligature traverses over the struts of the stent of the stent graft and, optionally, includes ligature sutures.

In another embodiment, shown in FIG. 8, ligature 86 traverses over at least one strut 89 of stent 88 of stent graft 82. It is understood that ligatures of the stent grafts of other embodiments of the delivery systems of the invention described above can also include ligatures that traverse an outside portion at least one strut of a stent of the stent graft. As shown in FIG. 8, ligature suture 87 secures ligature 86 to a position traversing the outwardly facing portion of struts 89 of stent 88.

Figure 9A:
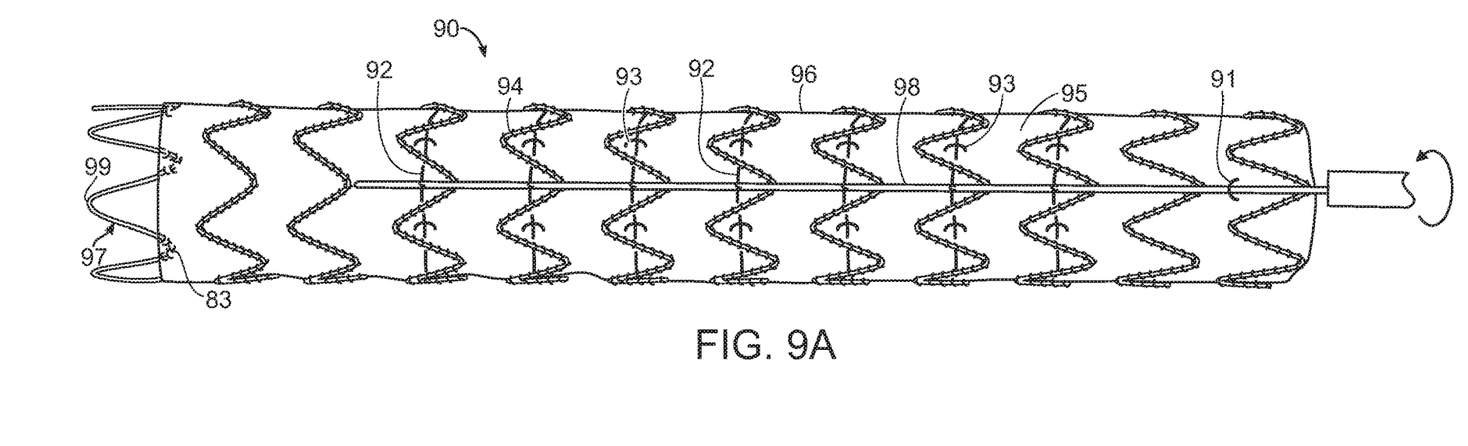
FIG. 9A is a side view of another embodiment of a stent graft delivery system of the invention, wherein a plurality of ligatures extend about the perimeter of radial stents at a stent graft, whereby rotation of a control rod of the stent graft will cause uniform radial constriction of the respective radial stents.
Figure 9B:
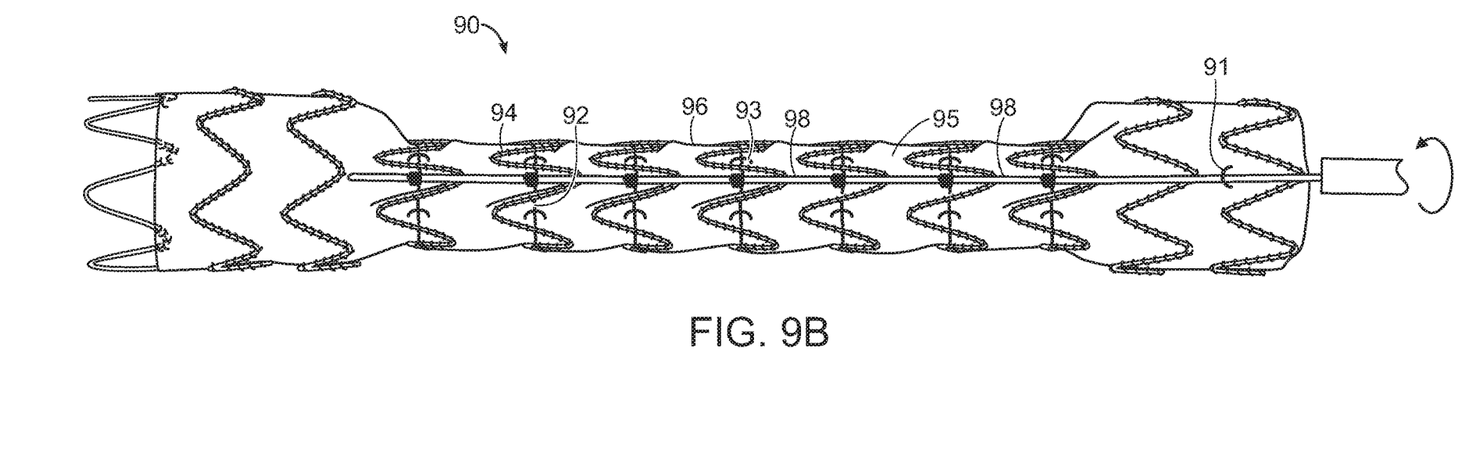
FIG. 9B is a side view of the stent graft delivery system of FIG. 8A, following rotation of the control rod to thereby radially constrict stents traversed by the ligatures linked to the control rod.

Another embodiment of a stent graft delivery system of the invention is shown in FIG. 9A. As shown therein, stent graft delivery system 90 includes a plurality of ligatures 92 that extend about the perimeter of stents 94 at stent graft 96, whereby rotation of control rod 98 of stent graft 96 causes uniform constriction of respective stents. In a method of the invention, represented by the transition from FIG. 9A to FIG. 9B axially rotating control rod 98 causes ligatures 92 to wrap around control rod 98, thereby radially constricting stents 94 traversed by ligatures 92 linked to control rod 98. Optionally, at least one loop 91 secures control rod 98 to luminal graft component 95 of stent graft 96. In a further embodiment, at least one loop 93 secures ligatures 92 to luminal graft component 95. Bare stent 97 is at the proximal open end and includes proximal apices 99 and distal apices 83, which, optionally, include barbs (not shown).

Figure 10A:
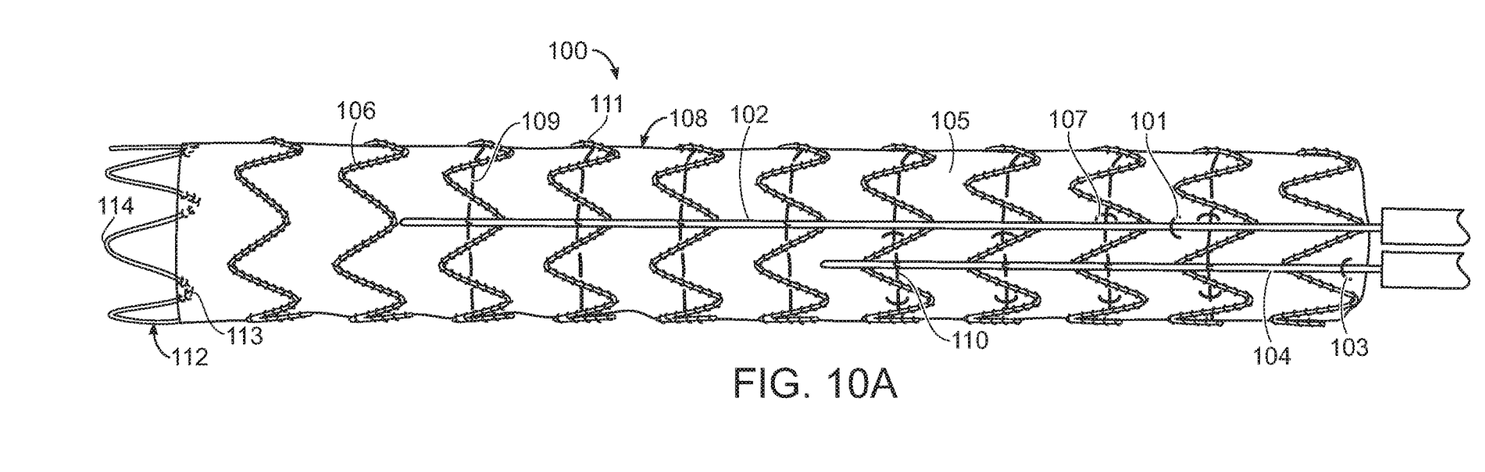
FIG. 10A is a side view of yet another embodiment of a stent graft delivery system of the invention, including a plurality of control rods that each separately and independently control radial constriction of different radial stents by independent axial rotation of the control rods.
Figure 10B:
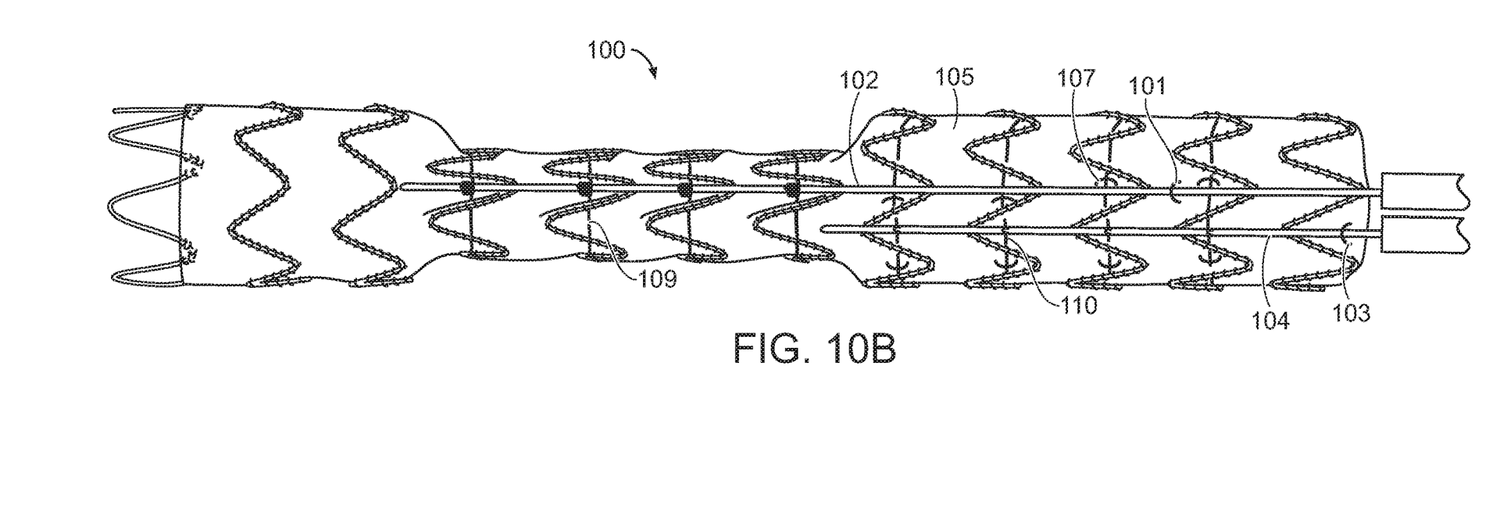
FIG. 10B is a side view of the stent graft delivery system shown in FIG. 10A, wherein a first control rod linked to ligatures at a first portion of radial stents has been axially rotated to thereby radial constrict the radial stents and the stent graft at the first portion of radial stents.
Figure 10C:
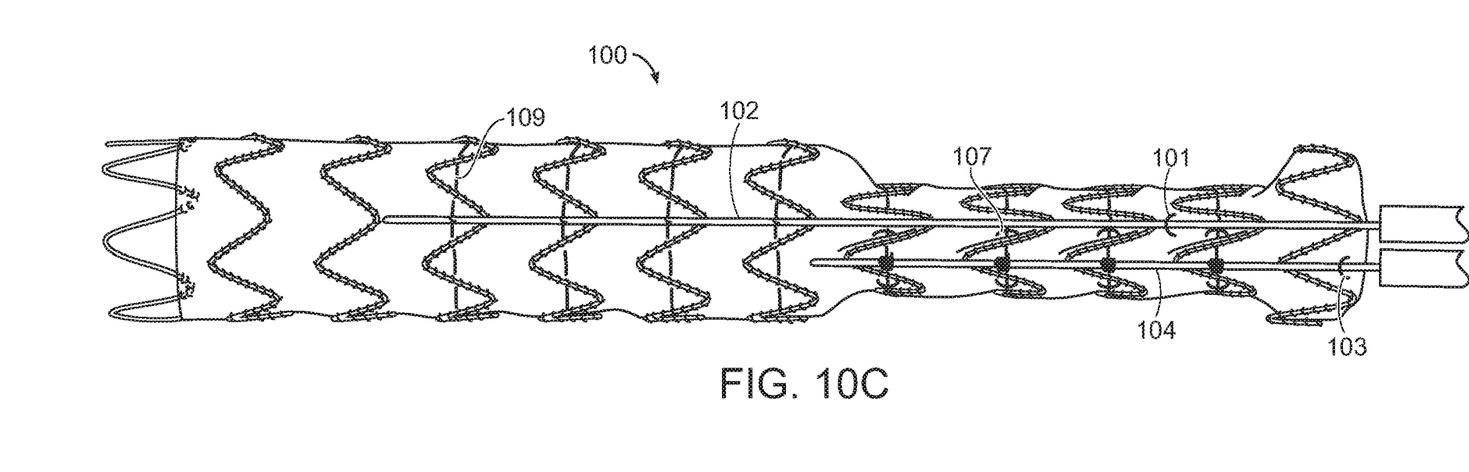
FIG. 10C is a side view of the stent graft delivery system shown in FIGS. 10A and 10B, wherein a second control rod linked to ligatures at a second portion of radial stents has been axially rotated to thereby constrict the second portion of radial stents and the stent graft at the second portion of radial stents independently of constriction of the first portion of radial stents.
Figure 10D:
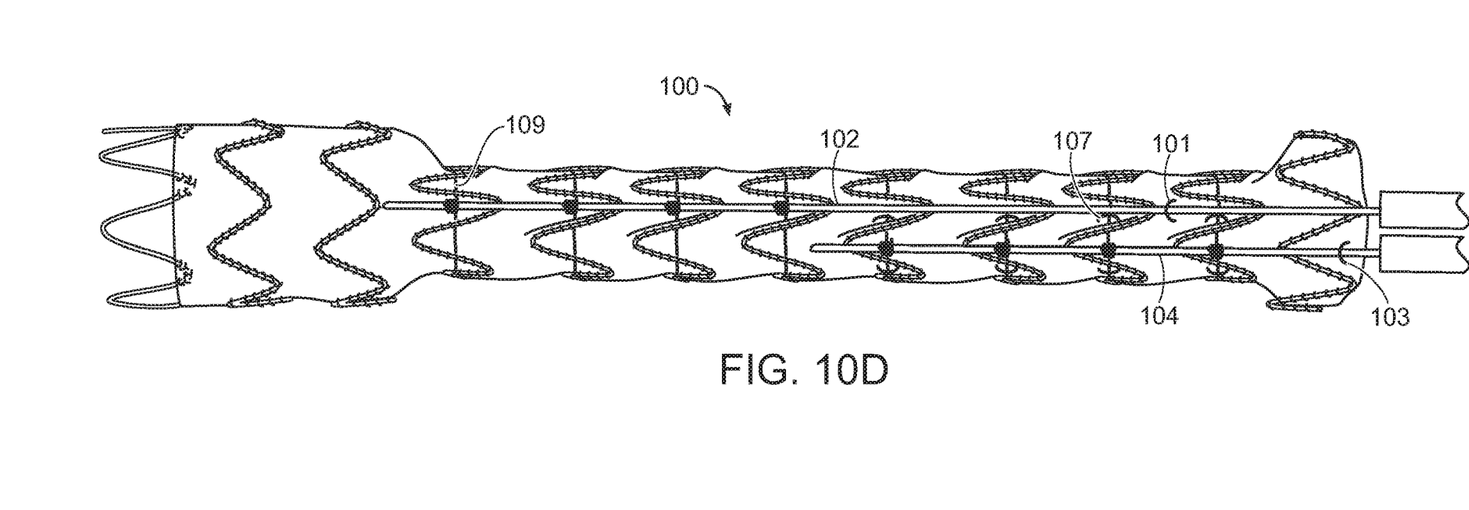
FIG. 10D is a side view of the stent graft delivery system shown in FIGS. 10A through 10C, wherein both the first and second control rods have been axially rotated to thereby constrict radial stents and the stent graft at the ligatures linked to the first and second control rods.

Another embodiment of a stent graft delivery system of the invention is shown in FIG. 10A. Stent graft delivery system 100 includes a plurality of control rods 102,104 each separately and independently control radial constriction of different portions or sets, of stents 106 of stent graft 108 by independent rotation of the control rods 102,104. For example, as can be seen in the transition from FIG. 10A to FIG. 10B, ligatures 109 and, therefore, first control rod 102, which is linked to ligatures at proximal portion of stents 111, is axially rotated to thereby radially constrict ligatures 109 and stent graft 108 at the proximal portion of stents 111 to a radially constricted position. Alternatively, as can be seen in the transition from FIG. 10A to 10C, axially rotating second control rod 104 linked to ligatures 110 at a distal portion of stents 111 radially constricts ligatures 110 and, therefore, stents and stent graft at the distal portion of stents 111 independently of radial constriction of the proximal portion of stents 111, thereby causing stent graft 108 at proximal portion of stents 111 to assume a radially constricted position. Bare stent 112 is at the proximal open end of the stent graft 108 and includes proximal apices 114 and distal apices 113 and, optionally, barbs at at least one of proximal apices 114 and distal apices 113 (not shown).

In yet another alternative, shown in the transition from FIG. 10A to FIG. 10D, both first control rod 102 and second control rod 104 are axially rotated to thereby radially constrict ligatures 109,110 and the proximal and distal portions of stents 111 and stent graft 108 at ligatures 109,110 linked to the first control rod 102 and second control rod 104, to cause stent graft 108 to be in a radially constricted position. Optionally, at least one of loops 101,103 secure at least one of first control rod 102 and second control rod 104, respectively, to luminal graft component 105 of stent graft 108. In a further embodiment, at least one loop 107 secures ligatures 110 of a second control rod 104 at the distal portion of stents 111 and at least one loop (not shown) secures ligatures 109 of first control rod 102 at the proximal portion of stents 111.

Although not shown, in another embodiment, the stent graft delivery system of the invention can include a plurality of control rods that each separately and independently control radial expansion of the same portion of stents, in particular a proximal portion of stents. The plurality of control rods are laterally and longitudinally arranged relative to each other about a circumference of the outside or inside surface of the luminal graft component (not shown). It is to be understood that control rods can be employed in the device and method of the invention to independently radially constrict various longitudinal portions of a stent graft, such as proximal and distal portions of a stent graft. It is also to be understood that a plurality of control rods can be distributed radially about a stent graft, either evenly, evenly in conjunction with a fenestration in the stent graft, or in another pattern or unevenly.

Figure 11:
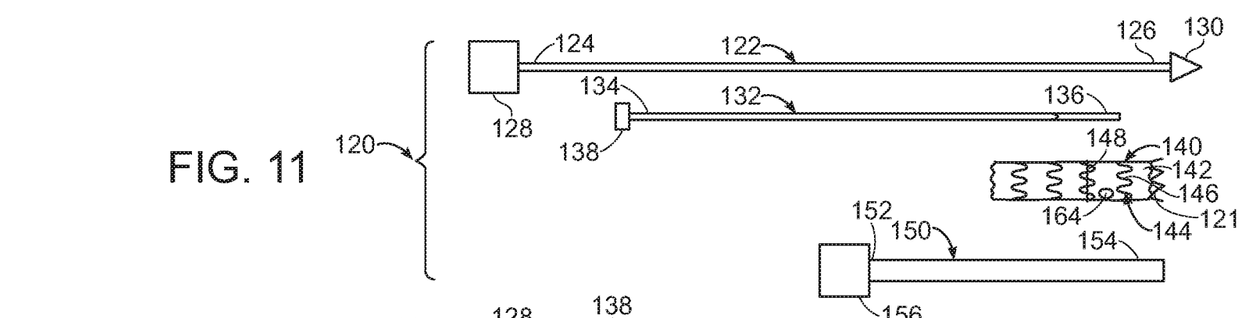
FIG. 11 is an exploded view of a stent graft delivery system of the invention and an embodiment of a stent graft for loading within an introducer sheath of the stent graft delivery system of the invention.

FIG. 11 is an exploded view of another embodiment of a stent graft delivery system of the invention. As shown therein, stent graft delivery system 120 includes guidewire catheter 122 having proximal end 124 and distal end 126. Proximal handle 128 is fixed to proximal end 124 of guidewire catheter 122. Nose cone 130 is fixed to distal end 126 of guidewire catheter 122. Control rod 132 includes proximal end 134 and distal end 136. Control rod handle 138 is fixed to proximal end 134 of control rod 132. Stent graft 140 includes luminal graft component 142 and stents 144. Stents 144 include struts 146 that define proximal and distal apices. Ligature 148 traverses struts of stent. Introducer sheath 150 includes proximal end 152 and distal end 154. Distal handle 156 is fixed to proximal end 152 of introducer sheath 150.

Figure 12A:
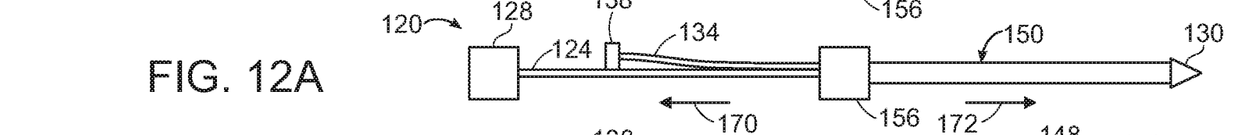
FIG. 12A is a side view of the stent graft delivery system shown in FIG. 11 when assembled, and preloaded with a stent graft (not shown).

FIG. 12A is a side view of the stent graft of the delivery system shown in FIG. 11, but when assembled, and wherein a stent graft 140 has been loaded within distal end 154 of introducer sheath 150. In an embodiment, stent graft 140 includes bare stent 121 at proximal open end 152 having proximal apices and distal apices that, optionally, include barbs.

Figures 12B, 12C:
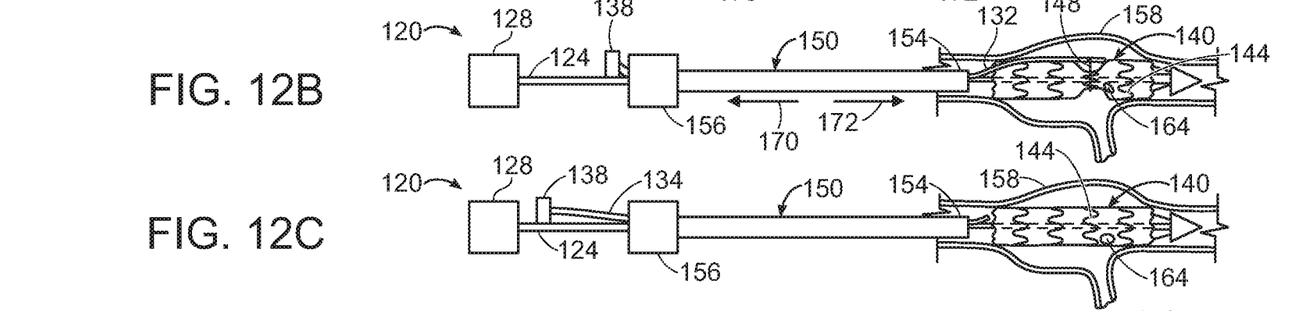
FIG. 12B is a side view of the stent graft delivery system shown in FIG. 12A, following retraction of an introducer sheath from about the stent graft at an arterial aneurysm site of a subject, but prior to release of a ligature radially constricting a radial stent of the stent graft by a control rod component of the stent graft delivery system of the invention.
FIG. 12C is a side view of the representation shown in FIG. 12B, following release of the control rod from the ligature at the radial stent of the stent graft, and retraction of the control rod from the stent graft at the aneurysm site.

FIG. 12B is a side view of a stent graft delivery system of FIGS. 11 and 12A, following direction of stent graft delivery system 120 to arterial aneurysm site 158 of a patient such as an aortic aneurysm, and location of stent graft 140 of stent graft delivery system 120 at a position spanning aneurysm site 158. As further shown in FIG. 12B, according to a method of the invention, stent graft 140 is located at arterial aneurysm 158, such as is shown in the transition between FIGS. 12A and 12B, and at least one stent 144 is radially constricted by ligature 148, which is wrapped about control rod 132 while stent graft 140 is positioned at arterial aneurysm 158 by the surgeon in the direction indicated by arrow 170. In the embodiment shown in FIG. 12B, stent graft 140 is exposed to aneurysm site 158 by retraction of distal handle 156 toward proximal handle 128 by the surgeon in the direction indicated by arrow 170. It is to be understood, however, that, alternatively, stent graft 140 can be advanced from within introducer sheath 150 at distal end 159 to arterial aneurysm 158 by advancing proximal handle 128 and control rod 132 toward distal handle 156 in the direction of arrow 172. In either case, the length of the portion of ligature 148 traversing stent can be increased or decreased controllable by axial rotation of control rod handle 138 and consequent rotation of control rod 132 by the surgeon during positioning of stent graft 140 at aneurysm 158. In one embodiment, stent graft 140 is positioned so that fenestration 164 at stent graft 140 is properly aligned with arterial branch 160 for subsequent placement of branch prosthesis 162 through fenestration 164 to arterial branch 160.

Upon completion of positioning of stent graft at aneurysm site 158, ligature 148 is released from control rod 132. Depending upon the embodiment of the control rod 132, as discussed above, for example, ligature 148 can be released from control rod 132 by proximally retracting control rod 132, as shown in the transition from FIG. 12B to FIG. 12C, or, by other means, such as by proximal retraction of a wire within a tube, as described above with reference to the embodiments of FIGS. 4A-4B and FIGS. 5-7C, thereby releasing ligature 148. Deployment of stent graft 140 then is complete.

Figure 12D:
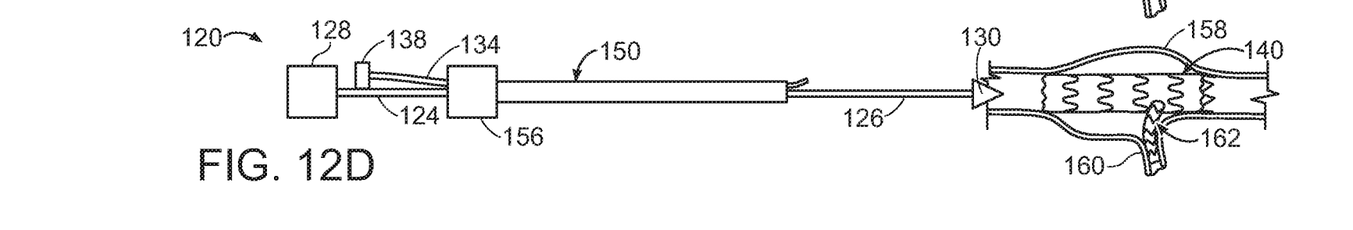
FIG. 12D is a side view of the embodiment shown in FIG. 12C, following proximal retraction of the stent graft delivery system from the stent graft, and following implantation of a branch prosthesis through a fenestration of a stent graft, thereby completing treatment of the arterial aneurysm by the method of the invention.

Thereafter, portions of stent graft delivery system 120 that are no longer linked to stent graft 140 are retracted from stent graft 140 and, if appropriate, branch prosthesis 162 is directed through stent graft 140 and fenestration 164 of stent graft 140 into arterial branch 160, thereby completing treatment of arterial aneurysm 158.

It is to be understood that ligature 148 can be adjusted not only by rotation of control rod 132, but maintained (in embodiments not shown) at a select position by fixing the position of control rod handle 138 by a suitable means, such as by biasing control rod handle 138 toward proximal handle 128 or distal handle 156, or by some other means. Bias of the control handle 138 can be obtained by a spring, friction, an interference fit or ratcheting between the control rod handle and another component of the delivery device, such as proximal handle 128 or distal handle 156.

Further, it is to be understood that, in other embodiments (not shown), a plurality of ligatures can be secured to control rod, whereby each ligature extends about a perimeter of a stent, whereby rotation of the control rod causes uniform constriction of the respective stents. It is also to be understood that more than a single control rod can be employed, whereby each control rod separately and independently controls a different stent.

Vascular prostheses implanted by the stent graft systems and methods of the invention can be implanted, for example, by transfemoral access. Additional branch prostheses that are directed into the vascular prostheses of the invention can be implanted, for example, by supraaortic vessel access (e.g., through the brachial artery), or by transfemoral access, or access from some other branch or branches of major blood vessels, including peripheral blood vessels.

The teachings of all patents, published applications and references cited herein are incorporated by reference in their entirety. The relevant teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112; 9,655,712; 9,827,123; 9,877,857; 9,907,686; U.S. patent application Ser. Nos. 14/575,673; 15/166,818; 15/167,055; 14/272,818; 14/861,479; 15/478,424; 15/478,737; 15/587,664; 15/604,032; 15/672,404; 15/816,772; 15/839,272; 15/417,467; PCT/US2017/025844; PCT/US2017/025849; PCT/US2017/025912; PCT/US2017/034223 and PCT/US2017/046062, are also incorporated by reference in their entirety.

The relevant teachings of International Patent Application Nos.: PCT/US2018/019355; PCT/US2018/019344; PCT/US/2018/019349; PCT/US2018/019353; PCT/US2018/019354; PCT/US2018/019352; PCT/US2018/019342; PCT/US2018/019350; PCT/US2018/019351; and PCT/US2018/019510, are also incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A stent graft delivery system, comprising:
a) a stent graft that includes
   i) a luminal graft component having an outside surface, an inside surface, a proximal open end, a distal open end, and defining a lumen, and
   ii) a plurality of stents extending longitudinally along the luminal wall;
b) a control rod extending longitudinally along the luminal graft component, wherein the control rod extends along the outside surface of the stent graft; and
c) at least one ligature traversing at least one of the stents and controllably and releasably fixed to the control rod, wherein the stent traversed by the ligature is radially self-expanding and includes struts that define apices, wherein the ligature traverses the struts of the stent, wherein the ligature passes through the luminal graft component and traverses the struts of the stent at portions of the ligature that are on the opposite side of the luminal graft component from the struts, whereby the radial constriction of the stent by the control rod is inherently reversible, and whereby control of the ligature at the control rod radially constricts the traversed stent.

2. The stent graft delivery system of claim 1, further including:
a) a guidewire catheter extending through the lumen of the stent graft, the guidewire catheter having a proximal end and a distal end;
b) a nose cone fixed to the distal end of the guidewire catheter;
c) a proximal handle at the proximal end of the guidewire catheter;
d) an introducer sheath that at least partially contains the stent graft and the control rod, the introducer sheath having a proximal end and a distal end; and
e) a distal handle at the proximal open end of the introducer sheath.

3. The stent graft delivery system of claim 2, wherein the ligature is controlled by axial rotation of the control rod, whereby the ligature wraps around the control rod to thereby control constriction of the traversed stent.

4. The stent graft delivery system of claim 3, wherein the control rod further includes a control rod handle at a proximal end of the control rod.

5. The stent graft delivery system of claim 4, wherein release of the control rod handle by the surgeon will cause the control rod handle to rotationally lock with the proximal handle or distal handle.

6. The stent graft delivery system of claim 5, wherein the control rod handle rotationally locks with either the proximal handle or the distal handle by at least one member of the group consisting of friction, an interference fit, and ratcheting.

7. The stent graft delivery system of claim 3, wherein the control rod includes a notch, whereby the ligature extends through the notch to thereby rotationally and releasably fix the ligature to the control rod.

8. The stent graft delivery system of claim 3, wherein the control rod defines a slot that extends longitudinally along a portion of the control rod, the ligature traversing the slot, thereby causing the ligature to be rotationally and releasably fixed to the control rod.

9. The stent graft delivery system of claim 3, wherein the control rod includes a luminal rod and a wire extending within the luminal rod, the luminal rod defining a transverse opening, and wherein the ligature extends between the luminal rod and the wire, whereby rotation of the luminal rod causes the ligature to wrap around the control rod.

10. The stent graft delivery system of claim 9, wherein the wire is retractable from within the luminal rod, thereby releasing the ligature.

11. The stent graft delivery system of claim 1, wherein the stent traversed by the ligature extends about the outside surface of the luminal graft component of the stent graft, and the ligature traverses the struts of the traversed stent at portions of the ligature that are at the inside surface of the luminal graft component.

12. The stent graft delivery system of claim 1, wherein the stent traversed by the ligature extends about the inside surface of the luminal graft component of the stent graft, and the ligature traverses the struts of the traversed stent at portions of the ligature that are at the outside surface of the luminal graft component.

13. The stent graft delivery system of claim 1, including a plurality of ligatures controllably and releasably fixed to the control rod and distributed along the control rod, wherein at least a portion of the ligatures each traverse a stent of the stent graft, whereby control of the ligature at the control rod constricts the traversed radially self-expanding stents in unison.

14. The stent graft delivery system of claim 1, including a plurality of control rods, and a ligature controllably and releasably fixed to each control rod, whereby constriction about respective traversed stents of the stent graft prostheses are independently controllable.

15. The stent graft delivery system of claim 1, wherein the control rod extends within the lumen of the luminal graft component.

16. The stent graft delivery system of claim 15, wherein the stent at the ligature includes struts that define apices, and wherein the ligature traverses the struts of the stent.

17. The stent graft delivery system of claim 16, wherein the ligature passes through the luminal graft component and traverses the struts of the stent at portions of the ligature that are on the opposite side of the luminal graft component from the struts.

18. The stent graft delivery system of claim 17, wherein the stent traversed by the ligature extends about the outside surface of the luminal graft component of the stent graft, and the ligature traverses the strut of the traversed stent at portions of the ligature that are at the inside surface of the luminal graft component.

19. The stent graft delivery system of claim 17, wherein the stent traversed by the ligature extends about the inside surface of the luminal graft component of the stent graft, and the ligature traverses the struts of the traversed stent at portions of the ligature that are at the outside surface of the luminal graft component.

20. The stent graft delivery system of claim 1, wherein the luminal graft component defines a fenestration.

21. The stent graft delivery system of claim 20, wherein the fenestration is bordered at least proximally or distally by the stents controlled by the ligature.

22. The stent graft delivery system of claim 21, wherein the fenestration is bordered both proximally and distally by stents controlled by the ligatures.

23. A stent graft delivery system, comprising:
a) a stent graft that includes
i) a luminal graft component having an outside surface, an inside surface, a proximal open end, a distal open end, and defining a lumen, and
ii) a plurality of stents extending longitudinally along the luminal wall;
b) a control rod extending longitudinally along the luminal graft component, wherein the control rod includes an external luminal rod defining an external fenestration, an internal luminal rod defining an internal fenestration aligned with the external fenestration, and a wire extending within the internal rod and traversing both the external and internal fenestrations of the control rod; and
c) at least one ligature traversing at least one of the stents and controllably and releasably fixed to the control rod, wherein the ligature traverses the aligned fenestrations of the external and internal luminal rods, and wherein the ligature extends between the internal and external luminal rods and the wire, whereby the stent graft can be constricted by at least one of retracting, advancing, and rotating the internal control rod relative to the external luminal rod, and released from the control rod by retracting the wire from the internal control lumen, whereby control of the ligature at the control rod radially constricts the traversed stent.

* * * * *